United States Patent
Reif

(10) Patent No.: US 8,895,763 B2
(45) Date of Patent: Nov. 25, 2014

(54) METHOD AND DEVICE FOR PRODUCING ALKYLENE OXIDES AND ALKYLENE GLYCOLS

(75) Inventor: Ferdinand Rudolf Reif, Zaberfeld (DE)

(73) Assignee: Thyssenkrupp UHDE GmbH, Dortmund (DE)

( * ) Notice: Subject to any disclaimer, the term of this patent is extended or adjusted under 35 U.S.C. 154(b) by 7 days.

(21) Appl. No.: 13/392,043

(22) PCT Filed: Aug. 12, 2010

(86) PCT No.: PCT/EP2010/004933
§ 371 (c)(1), (2), (4) Date: Apr. 23, 2012

(87) PCT Pub. No.: WO2011/023300
PCT Pub. Date: Mar. 3, 2011

(65) Prior Publication Data
US 2012/0203015 A1  Aug. 9, 2012

(30) Foreign Application Priority Data
Aug. 24, 2009  (DE) .......................... 10 2009 038 398

(51) Int. Cl.
| | |
|---|---|
| C07D 301/12 | (2006.01) |
| C07D 301/03 | (2006.01) |
| C07C 29/00  | (2006.01) |
| C07C 29/10  | (2006.01) |
| C07D 301/06 | (2006.01) |

(52) U.S. Cl.
CPC ............ *C07D 301/06* (2013.01); *C07C 29/106* (2013.01)
USPC ............ 549/531; 549/523; 568/866; 568/867

(58) Field of Classification Search
USPC .................................. 549/523; 568/866, 867
See application file for complete search history.

(56) References Cited

U.S. PATENT DOCUMENTS

| | | | |
|---|---|---|---|
| 3,574,772 A | 4/1971 | Becker et al. .................. | 260/637 |
| 3,674,813 A | 7/1972 | Bljumberg et al. ........... | 260/348 |

(Continued)

FOREIGN PATENT DOCUMENTS

| | | |
|---|---|---|
| CA | 2493707 A1 | 1/2004 |
| DE | 1 618 566 | 6/1971 |

(Continued)

OTHER PUBLICATIONS

International Preliminary Report on Patentability and Written Opinion.

(Continued)

*Primary Examiner* — T. Victor Oh
(74) *Attorney, Agent, or Firm* — Michael W. Ferrell

(57) ABSTRACT

An integrated process for preparing alkylene oxides and alkylene glycols is described. For this purpose, an alkylene oxide plant and an alkylene glycol plant are combined with one another and the water originating from the alkylene oxide plant and also other constituents of the reaction mixture are introduced into the alkylene glycol plant. In this way, alkylene glycols which have been produced in the alkylene oxide plant can be recovered as materials of value and the water circulation into the alkylene glycol plant can be eliminated or drastically reduced. In addition, the energy-intensive treatment of the process water from the alkylene oxide plant can be dispensed with. The integration of the two processes leads overall to better energy efficiency and conservation of resources in the work-up of residues from the process.

22 Claims, 1 Drawing Sheet

(56) References Cited

U.S. PATENT DOCUMENTS

| | | | | |
|---|---|---|---|---|
| 4,117,250 | A | 9/1978 | Foster et al. | 568/858 |
| 4,203,926 | A | 5/1980 | Wu et al. | 568/319 |
| 4,308,409 | A | 12/1981 | Wu et al. | 568/860 |
| 4,937,393 | A | 6/1990 | Masuda et al. | 568/867 |
| 5,306,847 | A | 4/1994 | Gehrer et al. | 568/863 |
| 6,765,101 | B1 * | 7/2004 | Bhasin et al. | 549/523 |
| 7,084,310 | B2 | 8/2006 | Bassler et al. | 568/867 |
| 7,332,634 | B2 | 2/2008 | Bassler et al. | 568/868 |
| 2008/0035468 | A1 | 2/2008 | Nakayama et al. | 203/53 |

FOREIGN PATENT DOCUMENTS

| | | | | |
|---|---|---|---|---|
| DE | 25 19 291 | 11/1976 | | C07C 69/28 |
| DE | 29 388 115 | 1/1981 | | C07C 31/20 |
| DE | 294 393 | 7/1987 | | C08G 65/28 |
| DE | 197 26 508 | 12/1998 | | C08G 65/28 |
| DE | 696 13 446 | 6/2001 | | C07D 301/32 |
| DE | 102 33 382 | 1/2004 | | C07C 29/80 |
| DE | 102 33 385 | 2/2004 | | C07C 29/10 |
| DE | 102 33 388 | 2/2004 | | C07C 29/80 |
| DE | 2004 054 047 | 5/2006 | | C07C 31/20 |
| DE | 2005 006 974 | 8/2006 | | C07C 67/08 |
| DE | 60 2004 010 144 | 9/2008 | | C07D 317/36 |
| DE | 10 2008 007 081 | 8/2009 | | C07C 11/2008 |
| EP | 0 226 799 | 7/1987 | | C07C 29/10 |
| EP | 0 761 797 | 3/1997 | | C09K 5/04 |
| EP | 1 527 057 | 7/2003 | | C07D 301/12 |
| EP | 1 658 279 | 11/2007 | | C07D 317/36 |
| EP | 2 070 902 | 6/2009 | | C07C 29/60 |
| WO | WO 02/088102 | 11/2002 | | C07D 301/04 |
| WO | WO 2004/009566 | 1/2004 | | C07D 301/12 |
| WO | WO 2004/009568 | 1/2004 | | C07D 301/12 |
| WO | WO 2004/085375 | 10/2004 | | C07C 68/06 |
| WO | WO 2007/027832 | 3/2007 | | C12P 7/18 |
| WO | WO 2008/071616 | 6/2008 | | B01J 27/045 |
| WO | WO 2008/071641 | 6/2008 | | C07C 29/00 |
| WO | WO 2009/001948 | 12/2008 | | C07D 301/04 |

OTHER PUBLICATIONS

Auma Ma?geschneiderte, "Wehweit ersle Anlagen ach dem HPPO-Vewrfahren von Evonik/Uhde Steht in Korea", http://www.process.vogel.de/anlagen apparatebau/engineering_dienstleistung/articles/141114/: Dipl.-Ing. Hans Jürgen Bittermann, Aug. 21, 2008; and Propylene oxide. Wikipedia. http//.en.wikipedia.org/wiki/Propylene_oxide.

Search Report from counterpart Taiwanese patent application dated Aug. 20, 2014.

* cited by examiner

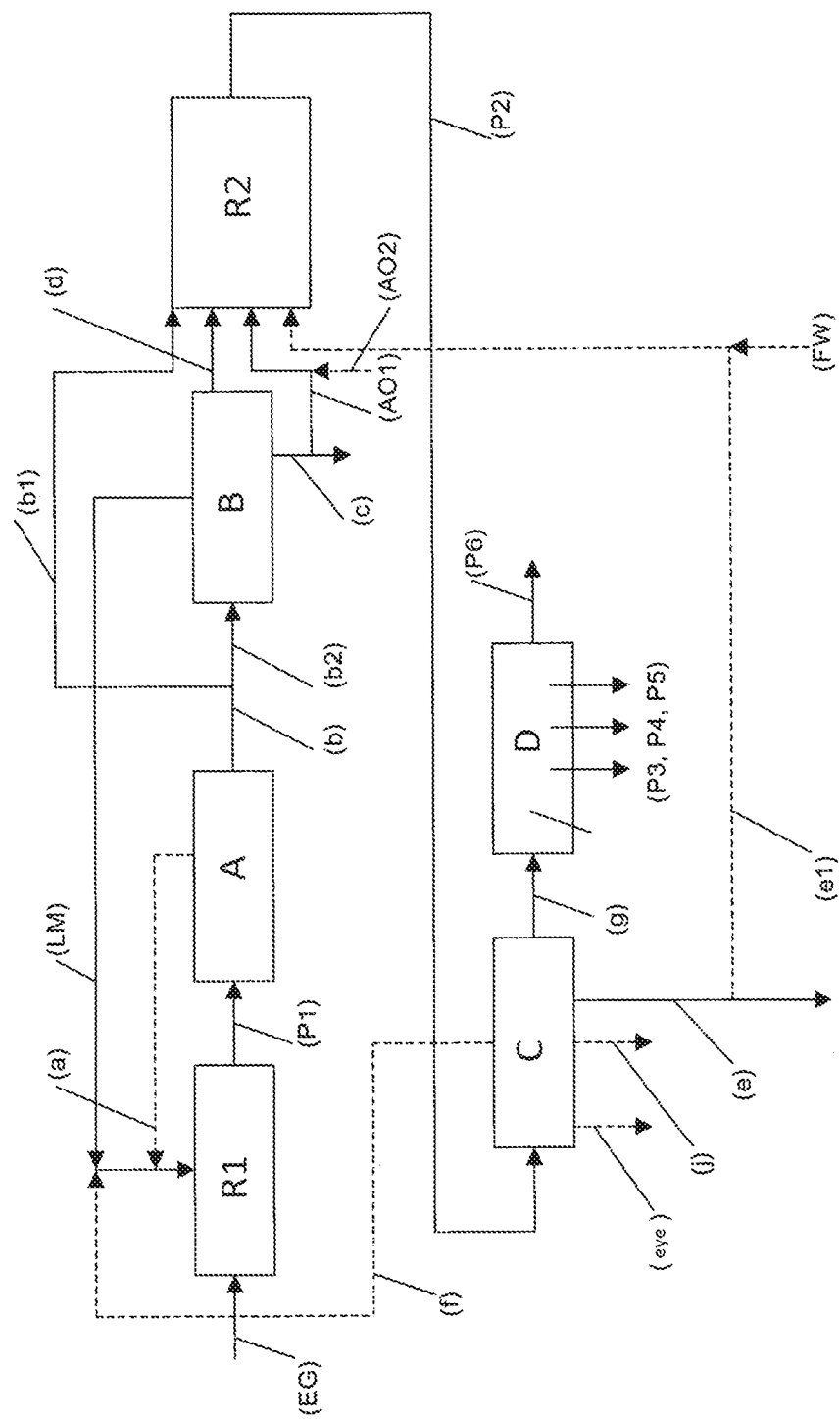

METHOD AND DEVICE FOR PRODUCING ALKYLENE OXIDES AND ALKYLENE GLYCOLS

CLAIM FOR PRIORITY

This non-provisional patent application is a national phase entry of International Patent Application No. PCT/EP2010/004933 (International Publication WO 2011/023300) filed on Aug. 12, 2010 and entitled "Verfahren und Vorrichtung zur Herstellung von Alkylenoxiden und von Alkylenglykolen". International Patent Application No. PCT/EP2010/004933 claims priority to German Application No. DE 10 2009 038 398.0, filed Aug. 24, 2009 of the same title. The priorities of International Patent Application No. PCT/EP2010/004933 and German Application No. DE 10 2009 038 398.0 are hereby claimed and their disclosures incorporated herein by reference in their entireties.

TECHNICAL FIELD

The present invention relates to a process for the combined preparation of alkylene oxides and alkylene glycols while simultaneously recovering the alkylene glycols formed as by-product during the preparation of alkylene oxide and also a plant matched to this process. Alternatively, the process may be carried out in such a way, or the plant may be operated in such a way that the resulting products are mainly alkylene glycol ethers rather than alkylene glycols.

BACKGROUND

The industrial preparation of alkylene oxides and alkylene glycols is generally known.

Alkylene oxides are usually obtained industrially by oxidation of alkenes. In the known industrially relevant processes, the corresponding alkylene glycols are formed as by-products by reaction with water present in the reaction system according to the exothermic reaction:

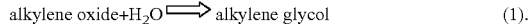
alkylene oxide+$H_2O$ ⇒ alkylene glycol (1).

In addition, subsequent reactions to form higher alkylene glycols such as dialkylene and trialkylene glycols take place according to the formulae:

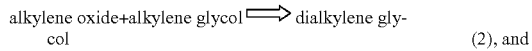
alkylene oxide+alkylene glycol ⇒ dialkylene glycol (2), and

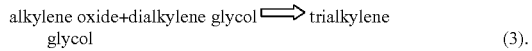
alkylene oxide+dialkylene glycol ⇒ trialkylene glycol (3).

In general, alkylene glycol concentrations of up to 10% are obtained here. These alkylene glycols are usually removed as high boilers together with the water from the alkylene oxide plant. Before release into the environment, this process water has to be purified, typically in a biological purification plant. The alkylene glycols present in this process water result in a very high COD value or a very high burden of biodegradable substances, so that the biological purification plant has to be made very large and the water generally has to be diluted beforehand. In addition, alkylene glycols are materials of value. As an alternative to an enlarged biological plant, the alkylene glycols can be removed by distillation, but this requires a high outlay in terms of energy and apparatus.

Alkylene glycols are obtained industrially by reaction of pure alkylene oxides in an aqueous phase corresponding to formulae (1), (2) and (3). The reactions according to (1), (2) and (3) take place at a considerable excess of water of, for example, about 10-20 times the stoichiometric amount. This water is generally removed from the reaction system in a first step by multistage vaporization and is, after condensation, fed back into the reactor. The alkylene glycol mixture formed is then separated into the individual glycols in a series of rectification columns. Due to the large amounts of water to be vaporized, large quantities of energy have to be introduced.

According to the invention, a conventional and known alkylene oxide plant and a conventional and known alkylene glycol plant are modified and combined with one another in such a way that both alkylene oxide and alkylene glycols or alternatively alkylene glycol ethers can be produced, the alkylene glycols and alkylene glycol ethers formed in the alkylene oxide plant are recovered as materials of value and the load on the downstream purification plant is thus also reduced, energy integration can take place, no fresh water has to be introduced and unpurified or only partially purified alkylene oxide can be used.

In addition, the preparation of alkylene oxides is frequently carried out in methanol as solvent. This has to be recovered after the reaction in order to be able to be recirculated to the process. Such a work-up process is described in DE 102 33 388 A1 (corresponding to WO 2004/009566 A1). Further processes for preparing alkylene oxides use other organic solvents. WO 2009/001948 A1 describes the reaction of propylene, hydrogen and oxygen to form propylene oxide in acetonitrile or in aqueous acetonitrile.

In conventional processes for preparing alkylene oxides, the starting material alkene is reacted in the liquid phase with an oxidant. The reaction can be carried out with addition of a catalyst. Oxidants which have been found to be useful are chlorine, hydroperoxides and preferably peroxides, particularly preferably hydrogen peroxide. The reaction takes place in a reactor, typically in a shell-and-tube reactor. In this, the alkene reacts with the oxidant to form alkylene oxide, possibly with formation of intermediates such as chlorohydrins which are subsequently converted into the alkylene oxide. Apart from the desired product alkylene oxide, alkylene glycols are formed to a small extent in the reaction. These compounds are, on the one hand, valuable chemicals but owing to the small amount can generally only be isolated with a high outlay in terms of apparatus and a high energy consumption, so that they have hitherto had to be disposed of in the work-up of the reaction residues. DE 102 33 382 A1 describes a process for the continuously operated pure distillation of the 1,2-propylene glycol obtained in the coproduct-free synthesis of propylene oxide. U.S. Pat. No. 7,332,634 B2 describes a continuous process for separating off 1,2-propylene glycol which is obtained as by-product in the preparation of propylene oxide.

The reactor for the preparation of the alkylene oxide is followed by separation of the reaction mixture into product, unreacted starting materials, water and any organic solvents present, typically in rectification columns. Low-boiling byproducts preferably leave the plant with the flushing gas while high-boiling by-products preferably leave the plant with the water used for dilution of the reactants or with the water formed in the reaction. This wastewater generally has to be diluted further before introduction into a biological wastewater treatment. An alternative approach separates organic compounds from the undiluted wastewater by distillation, so that less polluted wastewater is passed to the subsequent treatment stage. However, this requires a high consumption of energy.

Examples of the preparation of alkylene glycols from alkylene oxides may be found in WO 2004/085375 A1, EP 0 226

799 B1, U.S. Pat. No. 3,574,772, U.S. Pat. No. 4,937,393, DE 29 38 115 C2 and DE 197 26 508 A1. It is also possible to produce alkylene glycols from alkenes by direct reaction. Examples of this may be found in U.S. Pat. No. 4,203,926 and in U.S. Pat. No. 4,308,409.

In a conventional process for preparing alkylene glycols, the starting material alkylene oxide is mixed with water and passed through a reactor, typically a simple adiabatic tube reactor. In this, the alkylene oxide reacts with water in an exothermic reaction to form alkylene glycol. Apart from the simple alkylene glycol, higher alkylene glycols, i.e. mainly dialkylene glycol and trialkylene glycol and possibly also very small proportions of yet higher alkylene glycols, are generally formed. These compounds are likewise valuable chemicals. Typical ratios of alkylene glycol to dialkylene and trialkylene glycol are about 100:10:1. The reaction can be carried out with addition of a catalyst. The process employs large amounts of water which are generally circulated. These are necessary in order to remove the heat of reaction and to suppress the formation of higher alkylene glycols by diluting the alkylene oxide and the alkylene glycol.

After the reaction mixture has left the reactor, the water is firstly separated off, for example in a rectification column or in a simple evaporation. To save energy, a plurality of evaporators or rectification columns are frequently connected to one another.

The removal of water is followed by separation into the various alkylene glycols. This is generally carried out in rectification columns. Here, the alkylene glycol, the dialkylene glycol and finally the trialkylene glycol are separated off in order, in each case at the top or at the side offtake stream. High boilers present are taken off in the bottoms from the trialkylene glycol column and are generally discarded, for example by incineration. In some process variants, this third column is omitted because of the small amount of trialkylene glycol formed and the bottoms from the dialkylene glycol column are discharged from the plant and discarded. This process and this process variant are generally known.

Plants for the preparation of alkylene oxides and for the preparation of alkylene glycols have hitherto been operated separately although at present about 20% of the alkylene oxide produced is used for the preparation of alkylene glycols.

However, it has already been proposed that alkylene glycols and alkylene oxide be prepared in one plant and these products subsequently be separated from one another. An example of this may be found in WO 02/088102 A1. However, nonliquid and nonaqueous systems are used here and the reactions take place in the gas phase. The process has not been implemented industrially to the present time.

Combinations of plants in which various substances are reacted with one another and separated are already known. DE 10 2004 054 047 A1 describes a process for preparing 1,6-hexanediol from a carboxylic acid mixture comprising adipic acid, 6-hydroxycarboxylic acid and 1,4-cyclohexanediols by esterification of the carboxylic acid mixture, removal of the 1,4-cyclohexanediols by distillation, hydrogenation of the purified ester fraction and isolation of the 1,6-hexanediol by distillation. DE 10 2008 007 081 A1 describes a process for preparing n-butene oligomers and 1-butene from industrial mixtures of C4-hydrocarbons. Here, a starting material is firstly purified and worked up by distillation. A high boiler fraction obtained is subsequently reacted catalytically, resulting in the n-butenes present being oligomerized. DE 10 2005 006 974 A1 describes a continuous process for preparing cyclohexyl(meth)acrylate. Here, cyclohexanol is esterified with pure (meth)acrylic acid, neutralized, washed and subsequently purified by multistage distillation. In these processes and plants, neither alkylene oxide nor alkylene glycols are produced.

The coupling of a plant for preparing alkylene oxide with a plant for preparing alkylene glycol has also already been proposed. An example of this may be found in DE 102 33 385 A1 (which corresponds to WO 2004/009568 A1). Here, the alkylene glycol formed in the two plant sections is discharged from the respective plant section and combined in the workup of the alkylene glycols. In addition, fresh water is fed into the reactor for preparing alkylene glycol. The process described in these documents comprises coupling of the production of propylene oxide with the production of propylene glycols. However, the crude propylene oxide originating from the propylene oxide plant is reacted in the second reactor with water which does not originate from the first reactor. In addition, the propylene glycol mixtures obtained in the stages of propylene oxide production and propylene glycol production in the previously known process are combined and the individual propylene glycols are then separated off by distillation. Thus, in the previously known process, the reaction mixture which originates from the first reactor and has been freed of propylene and if appropriate of propylene oxide is conveyed past the second reactor and later combined with the propylene glycol mixture originating from the second reactor. This reaction mixture from the first reactor contains a considerable amount of water which essentially has to be removed either before or after this reaction mixture is combined with the propylene glycol mixture originating from the second reactor. Thus, the previously known process requires separate removal of the water from the first reactor and of the water from the second reactor, which results in a considerable outlay in terms of energy and capital costs since energy-intensive circulation of the water has to be carried out.

There is a continuing search for processes and measures by means of which the efficiency of these processes can be improved and by means of which these basic chemicals can be prepared more economically.

SUMMARY OF THE INVENTION

It is an object of the present invention to provide a simple and energy-efficient process for the combined preparation of alkylene oxides and of alkylene glycols and, if so desired, of alkylene glycol ethers and for the recovery of the alkylene glycols and alkylene glycol ethers formed in secondary reactions in the alkylene oxide plant and also a plant suitable for this purpose.

The present invention provides a process for preparing alkylene oxide and alkylene glycols in an integrated plant having a first subplant for preparing alkylene oxide by reacting $C_2$-$C_6$-olefin with an oxidant in a liquid and water-containing phase, where alkylene glycols and optionally alkylene glycol ethers are formed as by-products, and a second subplant for preparing alkylene glycols by reacting alkylene oxide with water in the liquid phase, which second subplant is connected to the first subplant, and the reaction mixture which comes from the first subplant and comprises at least water and alkylene glycols and possibly alkylene glycol ethers is introduced into the second subplant.

DETAILED DESCRIPTION

In the process of the invention, the alkylene glycol-containing and optionally alkylene glycol ether-containing process water stream from the alkylene oxide plant is, if appropriate after setting of a particular pH, introduced directly into the reactor of the alkylene glycol plant and after being separated off, for example by distillation, is discharged from the alkylene glycol plant. When the capacity is chosen appropriately, the energy-intensive recirculation of water can be dispensed with. If further valuable components are present in the wastewater, the wastewater can be subjected to a further treatment before being introduced into the wastewater treatment. The dewatered glycols are preferably separated by distillation into the monoalkylene glycol, dialkylene glycol and trialkylene glycol and if appropriate higher alkylene glycols. Since alkylene oxide plants and alkylene glycol plants are often operated on the same site, the invention is also suitable for reequipping and combining existing plants.

The reaction mixture which originates from the first subplant and comprises at least water, alkylene glycols and/or alkylene glycol ethers can either be introduced as such directly into the second subplant or one or more components, preferably the olefinic starting material, the reaction product alkylene oxide and, if used, the organic solvent, are preferably separated off from the reaction mixture before the latter is introduced into the second subplant.

In an alternative embodiment, the process of the invention can be operated so that mainly alkylene glycol ethers are formed in the second subplant. For this purpose, the reaction to form alkylene oxide in the first subplant is carried out in an aqueous-alcoholic solution and the reaction mixture which originates from the first subplant comprises at least water, alcohol, alkylene glycols and alkylene glycol ethers can either be introduced as such directly into the second subplant or one or more components, preferably the olefinic starting material and if appropriate the reaction product alkylene oxide, are preferably separated off from the reaction mixture before the latter is introduced into the second subplant. As a result of the introduction of relatively large amounts of alcohol into the second subplant, the alkylene glycols present or formed there are etherified or the alkylene oxide is reacted directly with alcohol to alkylene glycol ethers, so that the corresponding monoethers or diethers of the alkylene glycols are formed as main products.

The process of the invention enables a complicated work-up of the aqueous reaction mixture originating from the first subplant to be omitted since this mixture is introduced directly into the second subplant. A work-up of the water used and generated in the overall process and any organic solvent present can be dispensed with for the first subplant and can be entirely carried out after going through the second subplant. This makes possible a considerable saving of energy and capital costs.

The water discharged from the second subplant and any residual organic solvent present are preferably passed to a wastewater treatment. However, the water can also be partly circulated and at least some of it can be fed into the second subplant together with the water from the first subplant. Recirculation of the water originating from the second subplant is particularly preferred when operation of the first subplant has to be interrupted or scaled down. The organic solvent discharged from the second subplant can also be entirely or partly circulated after it has been separated off and at least part of it can be fed into the first subplant together with fresh organic solvent.

The alkylene glycols originating from the first subplant are combined in the second subplant with the alkylene glycols produced in the latter and worked up in the second subplant, preferably by rectification.

The alkylene glycol ethers originating from the first subplant are combined in the second subplant with the alkylene glycol ethers produced in the latter and are, after leaving the second subplant, either discharged with the water and, if appropriate after organic solvent has been separated off, then discarded or these alkylene glycol ethers are, as materials of value, separated off from the water and any organic solvent present after leaving the second subplant and then worked up, preferably by rectification.

If the reaction in the second subplant is carried out so that mainly alkylene glycol ethers are formed from the alkylene glycols present or formed therein, the alkylene glycol ethers originating from the first subplant are combined in the second subplant with the alkylene glycol ethers produced in the latter and are worked up in the second subplant, preferably by rectification.

In a preferred embodiment, the present invention provides a process for preparing alkylene oxide and alkylene glycols in an integrated plant having a first subplant for preparing alkylene oxide, which has at least one alkylene oxide reactor R1 and a downstream separation apparatus A and, if appropriate, a separation apparatus B downstream of A, which mainly comprise rectification columns, and, connected to the first subplant, a second subplant for preparing alkylene glycols, which has at least one alkylene glycol reactor R2 and at least one downstream separation apparatus C and at least one separation apparatus D located downstream of C, wherein the process comprises the following steps:

i) production of alkylene oxide by reaction of $C_2$-$C_6$-olefin with an oxidant in the liquid phase in the first subplant, ii) separation of the reaction mixture leaving the alkylene oxide reactor in the separation apparatus A into a substream "a" comprising essentially $C_2$-$C_6$-olefin and, if appropriate, further constituents of the reaction mixture which have been separated off with this and a substream "b" comprising water, alkylene oxide, alkylene glycol and further components of the reaction mixture and also, if appropriate, organic solvent, iii) if appropriate, separation of the substream "b" in the separation apparatus B into a substream "c" comprising essentially alkylene oxide and, if appropriate, further constituents of the reaction mixture which have been separated off with this and a substream "d" comprising water, alkylene glycol and further components of the reaction mixture and also, if appropriate, organic solvent, iv) production of alkylene glycol and higher alkylene glycols by reaction of alkylene oxide with water in the aqueous phase in the second subplant, by v) introducing the substream "b" from the separation apparatus A and/or the substream "d" from the separation apparatus B, if appropriate after adjusting the pH, into the alkylene glycol reactor R2, vi) introducing alkylene oxide from substream "c" and/or from other sources into the alkylene glycol reactor R2, with this step being able to be omitted if the substream "b" from the separation apparatus A is introduced into the alkylene glycol reactor R2, vii) separating the alkylene glycol- and, if appropriate, alkylene glycol ether-containing reaction mixture leaving the alkylene glycol reactor R2 in the separation apparatus C into a substream "e" consisting essentially of the water present in the reaction mixture and, if appropriate, further constituents of the reaction mixture which have been separated off with the water and also, if appropriate, additionally a substream "f" consisting essentially of the organic solvent present in the reaction mixture and, if appropriate, further constituents of the reaction mixture which have been separated off with the organic solvent and a substream "g" formed by the alkylene glycols and the other components of the reaction mixture which have not gone over into the substream "e" and, if appropriate, not into the substream "f" and also, if appropriate, into a substream "eye"[1] containing salts and other solids from the reaction mixture and, if appropriate, into a substream "j" containing monoalkylene glycol ether,

[1] Throughout this specification and claims, "eye" is used for this stream rather than "i", the minuscule form of the 9$^{th}$ letter of the alphabet, to avoid difficulties inherent in distinguishing "i" from "j" in certain typefonts—particularly on drawings.

viii) discharging at least part of the substream "e" from the plant and preferably introducing it into a wastewater purification plant and recirculating any remaining part of the substream "e" to the inlet of the alkylene glycol reactor R2, ix) recirculating any substream "f" present, if appropriate after further processing to the alkylene oxide reactor R1 and x) separating the alkylene glycols present in the substream "g" in the separation apparatus D.

The process of the invention is operated in a combination of two plants and allows a considerably simpler treatment of the process water formed in the plant. The amount of process water is also reduced since water is consumed by the reaction of the alkylene oxide to form alkylene glycols.

Advantageously, apart from an optional adjustment of the pH, no treatment of the process water coming from the first subplant is required since all or the major part of this is used in the second subplant. The process of the invention is distinguished from conventional processes in that the alkylene glycols formed as by-products in the first subplant pass through the second subplant and can be obtained as materials of value and in that a water circuit can be dispensed with in the second subplant or this water circuit can be made considerably smaller. Process water from the alkylene oxide plant is simply firstly mixed with alkylene oxide in the second subplant and subsequently fed directly to the alkylene glycol reactor. The water circuit is interrupted or greatly reduced. The process water which has been freed of alkylene glycol is not recirculated, or only a small part of it is recirculated, but instead fed to the biological wastewater treatment and does not have to be further diluted with water. The biological wastewater treatment can therefore be made smaller than in conventional plants.

For reasons of process economics, it is also advisable to provide the opportunity of water recirculation for the alkylene glycol plant so that this plant can continue production independently of the occurrence of process water. The first subplant can also only be operated with the alkylene glycol recovery in the second subplant while blocking the substream "d", for example.

The approach according to the invention has a number of advantages: it is generally advantageous to install an alkylene glycol plant downstream of the alkylene oxide plant since at least one substream of the alkylene oxide produced is then allowed to contain water. The alkylene oxide intended for the preparation of alkylene glycol therefore does not necessarily have to be taken off at the top of an alkylene oxide purification column but it is instead possible to use a side offtake stream. This makes it possible to save both capital costs (the part above the side offtake can be made smaller) and operating costs (a higher reflux ratio is necessary only for the water-free alkylene oxide). Should a molecular sieve be used for the removal of traces of water instead of an increased reflux ratio, only the part of the alkylene oxide for which "freedom from water" is desired has to be treated.

Further advantages are the abovementioned utilization of the alkylene glycol produced in the alkylene oxide synthesis, the simpler wastewater treatment, the direct use of the reaction energy for vaporization of the wastewater and also the reduction in the amount of wastewater.

In a preferred embodiment of the process of the invention, no separate wastewater treatment is necessary for the processing wastewater mixture from the first subplant; the process water from the first subplant is transferred in its entirety into the second subplant and is treated in a wastewater purification plant downstream of the second subplant.

The two subplants require no great modifications compared to individually operating plants. Compared to an isolated alkylene oxide plant with downstream wastewater treatment, only part of the second plant section is additionally required for the process of the invention. This is essentially the reactor for the preparation of alkylene glycol and the separation apparatuses for the dialkylene and trialkylene glycols, which can be made comparatively small because of the good separability of the monomeric, dimeric and trimeric alkylene glycols and the low mass flows.

In the first subplant, any processes for preparing alkylene oxides from alkenes and oxidants can be operated. Known industrial processes are the chlorohydrin process, the Prilezhaev reaction and the HPPO process.

In the chlorohydrin process, alkene is reacted with chlorine to form the corresponding chlorohydrin and part of the chlorohydrin is converted in a basic aqueous phase into alkylene oxide. In the Prilezhaev reaction, an alkene is converted into the alkylene oxide by reaction with a hydroperoxide. In the HPPO process, an alkene is reacted with a peroxide, preferably hydrogen peroxide, to form alkylene oxide.

In the process of the invention, $C_2$-$C_6$-olefins are used. Preference is given to using alpha-olefins. Examples are ethylene, propylene, alpha-butene, alpha-pentene or alpha-hexene.

The process of the invention is particularly preferably used for preparing ethylene oxide and ethylene glycols such as ethylene glycol, diethylene glycol and triethylene glycol.

The process of the invention is very particularly preferably used for preparing propylene oxide and propylene glycols such as propylene glycol, dipropylene glycol and tripropylene glycol.

The alkylene oxide is produced in the liquid phase. The oxidant is preferably used in aqueous or in aqueous-alcoholic solution, for example as aqueous solution of a peroxide, e.g. hydrogen peroxide, or a hydroperoxide, e.g. benzoyl hydroperoxide. The actual reaction proceeds in the liquid phase. Possibilities here are preferably water or water-miscible organic polar liquids, in particular alcohols. Particular preference is given to using methanol. The reaction system can, depending on the concentration of the individual constituents, consist of one or more phases. Thus, for example, an aqueous solution of the oxidant with an alcohol as solvent together with the starting material can form a single-phase or two-phase reaction mixture. In addition, a catalyst is generally also used; this can be suspended as solid in the reaction mixture and/or be arranged in the form of a solid bed.

In a preferred variant of the process of the invention, propylene is reacted catalytically with a peroxide or hydroperoxide in the liquid, preferably in the aqueous or aqueous-alcoholic phase to form propylene oxide in step i). Very particular preference is given to using hydrogen peroxide as oxidant. Particular preference is likewise given to carrying out the reaction in methanol.

The first plant section preferably comprises an alkylene oxide reactor R1 for the reaction to form alkylene oxide and a separation apparatus A for recovering the unreacted starting material and, if appropriate, further constituents of the reaction mixture which can be separated off with the starting material, e.g. organic solvent and water, and, if appropriate, a separation apparatus B for separating the alkylene oxide formed from water and from any organic solvent present, e.g. methanol, located downstream of the separation apparatus A, and also from further constituents of the reaction mixture.

Any alkylene oxide reactors can be used in the first subplant. It is possible to use one or more such reactors which can be connected in parallel or in series. In the first subplant, preference is given to using an alkylene oxide reactor, very particularly preferably two or three alkylene oxide reactors connected in series. If "the" or "an alkylene oxide reactor" is spoken of below in the present description, this should be understood to mean one or more alkylene oxide reactors connected in any way.

Any separation apparatuses A and, if appropriate, B can be used in the first subplant. The separation apparatuses can comprise one or more units; these can be connected in parallel or in series. Preference is given to using separation apparatuses A and B which each comprise a plurality of units in the first subplant.

Alkylene oxide reactors R1 which are preferably used are shell-and-tube reactors. Separation apparatuses A and/or B which are preferably used are rectification columns. The separation apparatuses A and B preferably each comprise one or more rectification columns. Thus, in a preferred process variant, the unreacted starting material can firstly be separated off from the reaction mixture in a separation apparatus A, which is in this case configured as a rectification column. The olefin which has been separated off can contain further constituents of the reaction mixture which have a boiling point similar to that of the olefin or form an azeotrope with the latter. These constituents can be separated off from the olefin in a downstream rectification column or another purification stage; the olefin is then preferably recirculated to the alkylene oxide production process and the separated-off constituents are preferably passed to incineration.

After the olefin has been separated off from the reaction mixture, the latter is then preferably purified further in a further series of rectification columns as separation apparatus B. As an alternative, this stage can be omitted and the reaction mixture which has been freed of the olefin can be fed directly into the alkylene glycol reactor. However, a separation apparatus B is preferably used. However, preference is given to using a separation apparatus B. In a rectification column, the alkylene oxide formed is separated off as overhead product and/or as side off take stream (substream "c"), if appropriate with further constituents of the reaction mixture having a similar boiling point or with azeotrope-forming constituents. In a further rectification column, the major part of the organic solvent (e.g. methanol) is preferably separated off from the remaining reaction mixture and subjected to a further distillation, e.g. in a further rectification column, to separate off the organic solvent from the water and from further constituents of the reaction mixture. The organic solvent recovered in this way is preferably recirculated (substream "LM") to the alkylene oxide reactor R1. The bottom product from this rectification column generally comprises water as the main constituent, together with organic solvent, salts, catalyst residues, intermediate- and high-boiling organic constituents and alkylene glycols formed in the alkylene oxide preparation and possibly alkylene glycol ethers as additional constituents. The bottom product in this preferred process variant is fed as substream "d" into the alkylene glycol reactor R2, with water obtained in the preceding stages of the work-up being able to be added to this substream "d".

Preference is given to introducing at least part of the alkylene oxide formed in the alkylene oxide reactor R1 into the alkylene glycol reactor R2 of the second subplant.

In an alternative process variant, part of the substream "b" from the separation apparatus A and/or an organic solvent can be fed directly into the alkylene glycol reactor R2 and the remainder of the substream "b" is subjected to a further work-up in the separation apparatus B, with the substream "d" obtained here likewise being able to be introduced into the alkylene glycol reactor R2.

In a further alternative process variant, water and organic solvent are not separated in the separation apparatus B but these two materials are instead introduced together into the alkylene glycol reactor R2. This process variant is preferably employed when not only alkylene glycols but also a high proportion of alkylene glycol ethers are wanted as material of value.

In a preferred process variant, a series of rectification columns is used as separation apparatus B and, in one of these columns, part of the alkylene oxide is taken off at the top of the column, a further part is taken off as side off take stream and at least one bottom product forms the substream "d".

The oxidant which has not been reacted in the alkylene oxide reactor R1, preferably the unreacted peroxide, in particular the unreacted hydrogen peroxide, is preferably destroyed by addition of a reducing agent or a decomposition catalyst between the alkylene oxide reactor R1 and the alkylene glycol reactor R2. For this purpose, an apparatus for destroying oxidant which has not been reacted in the alkylene oxide reactor is located between the alkylene oxide reactor and the alkylene glycol reactor R2. This apparatus can be installed at various positions between the alkylene oxide reactor R1 and the alkylene glycol reactor R2. If the substream "b" and/or the substream "d" contains large amounts of organic solvent, e.g. methanol, and this is separated off from the corresponding substream before the latter is introduced into the alkylene glycol reactor R2, the apparatus for destroying unreacted oxidant is located upstream of the apparatus for separating off the organic solvent.

In the second subplant, any processes for preparing alkylene glycols and optionally alkylene glycol ethers from alkylene oxides can be operated. In general, these are reactions of alkylene oxide with water in a neutral, basic or acidic medium. These processes are preferably carried out without the use of catalysts or with the use of acidic catalysts such as acids, for example, mineral acids or acidic ion exchange resins. Such processes and catalysts suitable for them are known to those skilled in the art.

If not only the formation of alkylene glycols but also mainly the further reaction to alkylene glycol ethers is desired in the second subplant, this is preferably carried out in an aqueous-alcoholic medium, preferably in an aqueous-methanolic medium containing an excess of methanol. The reaction can in this case also be carried out at acidic, neutral or basic pH values.

Preference is given to a process in which the substream "d" from the separation apparatus B and/or the substream "b" from the separation apparatus A or a part thereof is combined with part of the substream "e" from the separation apparatus C, i.e. the apparatus for separating off water before it is introduced into the alkylene glycol reactor R2.

Furthermore, preference is given to a process in which the substream "b" and/or an organic solvent is/are introduced into the alkylene glycol reactor R2 and in which the separation of the reaction mixture which leaves the alkylene glycol reactor R2 and contains alkylene glycols and optionally alkylene glycol ethers is carried out in the separation apparatus C in such a way that the substream "e" consists essentially of the water present in the reaction mixture and if appropriate ethers which have been formed from part of the alkylene oxide and other constituents of the reaction mixture and in which the substream "f" consists essentially of the organic solvent present in the reaction mixture and if appropriate ethers which have been formed from part of the alkylene oxide and other constituents of the reaction mixture.

The alkylene oxide required for the preparation of the alkylene glycols can originate from any sources. Preference is given to a process in which the alkylene oxide fed into the alkylene glycol reactor R2 comes entirely or partially from the first subplant.

Any alkylene glycol reactors R2 can be used in the second subplant. It is possible to use one or more such reactors which can be connected in parallel or in series. In the second subplant, preference is given to using an alkylene glycol reactor R2, very particularly preferably two or three alkylene glycol reactors R2 which are connected in series. If "the" or "an alkylene glycol reactor" is spoken of below in the present description, this should be understood to mean one or more alkylene glycol reactors R2 connected in any way.

Any separation apparatuses C and D can be used in the second subplant. The separation apparatuses can comprise one or more units; these can be connected in parallel or in series. Preference is given to using separation apparatuses C and D which in each case comprise a plurality of units in the second subplant.

Preferred alkylene glycol reactors R2 are tube reactors. Preferred separation apparatuses C and D are rectification columns. In the case of the separation apparatuses C, thin-film evaporators are also preferably used. There can also be used combinations of rectification columns and thin-film evaporators.

The reaction mixture discharged from the alkylene glycol reactor is subsequently freed of the water present therein and, if appropriate, of salts and other solids present therein in the separation apparatus C. Depending on the separation technique used, further constituents present in the reaction mixture, e.g. the organic solvent used in the reaction and by-products, can be present in the water separated off, for example in the case of separation by distillation components having a boiling point similar to that of water or components which form an azeotrope with water. It is important that none of the valuable alkylene glycol or only very small amounts thereof is/are present and—if it is also the aim to generate alkylene glycol ethers—that none of the valuable alkylene glycol ether or only very small amounts is/are present in the water separated off. The water can be separated off from the reaction mixture discharged from the alkylene glycol reactor by distillation, preferably in rectification columns, or by means of membrane filtration or by means of other suitable separation techniques. The water separated off combined with any further constituents of the reaction mixture separated off therewith forms the substream "e". The salts and other solids which may be separated off combined with further constituents of the reaction mixture separated off therewith form the substream "eye". Any alkylene glycol ethers present can be partly separated off in this stage; mainly monoalkylene glycol ethers are separated off and form the substream "j". The higher alkylene glycol ethers are obtained mainly in the alkylene glycol fraction where they may be separated off later.

The separation apparatus C for separating off the water from the reaction mixture discharged from the alkylene glycol reactor R2 preferably comprises a plurality of rectification columns which are connected in parallel and also preferably comprises at least one downstream rectification column. In the rectification columns connected in parallel, in each case, parts of the reaction mixture discharged from the alkylene glycol reactor R2 are introduced. Heat energy from the top of at least one rectification column is utilized, in a particularly preferred embodiment, for heating the bottom of at least one other rectification column and the rectification columns are operated at different pressures so that the overhead product in each case comprises water and organic constituents. As an alternative, part of the heat energy can be used for heating other columns in the first subplant and/or the second subplant, for example for heating columns for separating the alkylene glycols. The water-containing overhead products from the rectification columns connected in parallel are preferably introduced into the downstream rectification column where the remaining water is separated off.

If the substream "b" and/or the substream "d" containing, inter alia, larger amounts of organic solvent have been introduced into the alkylene glycol reactor R2 and/or if organic solvent originating from other sources was added to the alkylene glycol reactor R2, not only water but also the organic solvent are preferably separated off from the reaction mixture in the separation apparatus C. The organic solvent can be separated off before or after the water has been separated off. Here too, further constituents present in the reaction mixture, e.g. water or by-products, can, depending on the separation technique used, be present in the organic solvent which has been separated off, for example in the separation by distillation of components having boiling points similar to that of the organic solvent. Here too, it is important that no valuable alkylene glycol or very small portions of alkylene glycol and, if appropriate, alkylene glycol ether, are present in the organic solvent separated off. The separation of the organic solvent from the reaction mixture discharged from the alkylene glycol reactor R2 can likewise be carried out by distillation, preferably in rectification columns, or by means of membrane filtration or by means of other suitable separation techniques. The organic solvent separated off forms the substream "f".

In a preferred process variant, the fractionation of the reaction mixture containing alkylene glycols which leaves the alkylene glycol reactor R2 is carried out in the separation apparatus C in such a way that the substream e consists essentially of the water present in the reaction mixture and possibly small amounts of organic solvent and ethers which have been formed from parts of the alkylene oxide and other constituents of the reaction mixture.

The water which has been separated off as substream "e" is either entirely discharged from the plant and, for example, passed to a biological wastewater purification or part of the water separated off is recirculated to the inlet of the alkylene glycol reactor R2 and combined with the water from the substream "b" and/or from the substream "d" coming from the first plant section. Any substream "eye" which has been separated off is discharged from the plant for disposal. Any substream "j" which has been separated off is used as material of value or subjected to a further work-up.

In a further preferred process variant, the fractionation of the reaction mixture containing alkylene glycols leaving the alkylene glycol reactor R2 is carried out in the separation apparatus C in such a way that a substream "e" and also a substream "f" which consists essentially of the organic solvent present in the reaction mixture and possibly small amounts of water and ethers which have been formed from parts of the alkylene oxide and other constituents of the reaction mixture are produced. If appropriate, salts and further solids, e.g. catalyst constituents, can be separated off in this separation stage C and then form the substream "eye", or it is possible to separate off monoalkylene glycol ethers which form the substream "j".

In a particularly energy-efficient variant of the process of the invention, the separation apparatus C has at least one rectification column in which the major part of the water present, preferably from 90 to 98% of the water present, is separated off and there is also a further rectification column in which the remainder of the water is separated off.

The organic solvent separated off as substream "f" is recirculated to the alkylene oxide reactor R1, either directly or preferably after further purification.

The substream "g" which remained after separation of the substream "e", if appropriate, of the substream "eye" and/or "j" and, if appropriate, of the substream "f", contains alkylene glycols and, if appropriate, alkylene glycol ethers as materials of value. This stream is a mixture of various alkylene glycols and, if appropriate, various alkylene glycol ethers and further constituents of the reaction mixture, for example salts, organic by-products and catalyst residues. The separation of the alkylene glycols and of any alkylene glycol ethers present can be carried out by any method known to those skilled in the art. Rectification columns are generally used for this purpose.

In a further preferred process variant, a separation apparatus for alkylene glycol having a plurality of stages connected in series is used, with the alkylene glycol being separated off in the first stage, the dialkylene glycol being separated off in the second stage and the trialkylene glycol being separated off in an optionally present third stage, if appropriate, together with further intermediate or high boilers, and the bottom product remaining in the last stage being discharged from the plant.

If the substream "g" to be purified contains relatively large proportions of alkylene glycol ethers in addition to alkylene glycols, these ethers can likewise be separated off in the separation apparatus for alkylene glycols having a plurality of stages connected in series. When alkylene glycol ethers are present, further stages can be provided. The bottom product remaining in the last stage is discharged from the plant.

Particular preference is given to a process in which a separation apparatus D for alkylene glycol and for alkylene glycol ethers is used, with the alkylene glycol and, if appropriate, dialkylene glycol ethers being separated off in the first stage, the dialkylene glycol being separated off in a second stage, trialkylene glycol ethers being separated off in a third stage, the trialkylene glycol, if appropriate together with further intermediate or high boilers, being separated off in a fourth stage which may optionally be present and the remaining bottom product being discharged from the plant.

The stages for the separation of the alkylene glycols and, if appropriate, the alkylene glycol ethers, are preferably rectification columns connected in series.

As an alternative, the alkylene glycols can be separated in one rectification column having overhead and side offtakes. For the purposes of the present description, the term rectification column also encompasses dividing wall columns.

The invention likewise provides a plant for preparing alkylene oxide and alkylene glycols and, if appropriate, alkylene glycol ethers, which comprises the following elements:
A) first subplant for preparing alkylene oxide,
B) second subplant for preparing alkylene glycols and, if appropriate, alkylene glycol ethers, where
the first subplant is connected to the second subplant and has at least one line through which the reaction mixture which originates from the first subplant and comprises at least water, alkylene glycols and alkylene glycol ethers is introduced into the second subplant.

In a preferred embodiment, the invention provides a plant for preparing alkylene oxide, alkylene glycols and if appropriate alkylene glycol ethers comprising elements A) and B) as defined above as well as elements C) to F), where
C) the first subplant comprises at least one alkylene oxide reactor R1 and also a downstream separation apparatus A for separating the reaction mixture leaving the alkylene oxide reactor R1 into a substream "a" comprising essentially $C_2$-$C_6$-olefin and possibly further constituents of the reaction mixture which have been separated off with the olefin and a substream "b" containing water, alkylene oxide, alkylene glycol and further components of the reaction mixture and also, if appropriate, organic solvent and, if appropriate, a separation apparatus B downstream of the separation apparatus A for separating the substream "b" into a substream "c" comprising essentially alkylene oxide and possibly further constituents of the reaction mixture which have been separated off with the alkylene oxide and a substream "d" containing water, alkylene glycol and further components of the reaction mixture and also, if appropriate, organic solvent,
D) the second subplant comprises at least one alkylene glycol reactor R2 and also at least one downstream separation apparatus C and, downstream thereof, at least one separation apparatus D, where the reaction mixture leaving the alkylene glycol reactor R2 is separated in the separation apparatus C into a substream "e" consisting essentially of the water present in the reaction mixture and possibly further constituents of the reaction mixture which have been separated off with the water and, if appropriate, additionally a substream "f" consisting essentially of the organic solvent present in the reaction mixture and possibly further constituents of the reaction mixture which have been separated off with the organic solvent and a substream "g" formed by the alkylene glycols and the other parts of the reaction mixture which have not gone over into the substream "e" and not gone over into the substream "f" and, if appropriate, into a substream "eye" containing salts and other solids from the reaction mixture and/or, if appropriate, into a substream "j" containing monoalkylene glycol ether,
E) the alkylene glycol reactor R2 has at least one line for the introduction of alkylene oxide, where this line can be omitted if the substream "b" is fed into the alkylene glycol reactor R2, and F) at least one line AO1 through which at least part of the substream "b" and/or the substream "d" from the first subplant is introduced into the alkylene glycol reactor R2 of the second subplant is provided.

The subplants are, as indicated above, known to those skilled in the art and consist of known components. The connection of these plants to form an integrated plant has not been described hitherto.

In a preferred variant of the plant of the invention, an apparatus in which the oxidant which has not been reacted in the alkylene oxide reactor R1 is destroyed is provided between the alkylene oxide reactor R1 and the alkylene glycol reactor R2.

In a preferred embodiment of the plant of the invention, a line through which at least part of the substream "e" is brought to a wastewater purification plant is provided.

In a further preferred embodiment of the plant of the invention, a line through which at least part of the substream "f" is, preferably after further purification, recirculated to the alkylene oxide reactor R1 is provided.

In a further preferred embodiment of the plant of the invention, a line through which at least part of the substream "a" is recirculated to the alkylene oxide reactor R1 is provided.

In a further preferred embodiment of the plant of the invention, a first line through which at least part of the substream "b" is introduced into the alkylene glycol reactor R2 and a second line through which at least part of the substream "e" is recirculated to the inlet of the alkylene glycol reactor R2 are provided.

In a further preferred embodiment of the plant of the invention, a line through which salts and other solids present in the reaction mixture are discharged from the plant as substream "eye" is provided.

In a further preferred embodiment of the plant of the invention, a line through which monoalkylene glycol ether is discharged from the plant as substream "j" is provided.

Particular preference is given to a plant which has a first line through which at least part of the substream "b" is introduced into the alkylene glycol reactor R2 and a second line through which at least part of the substream "e" is recirculated to the inlet of the alkylene glycol reactor R2 and in which means allowing the amount of the substreams introduced via said first and second lines into the alkylene glycol reactor to be regulated are provided.

In a preferred plant, the separation apparatus A is at least one flash vessel or at least one vaporizer in which the olefin is taken off, if appropriate together with other low boilers, and the residue forms the substream "b".

In a preferred plant, the separation apparatus B is a rectification column or a group of rectification columns connected to one another, in which the alkylene oxide is taken off at the top of the column and, if appropriate, additionally as side offtake stream and in which a bottom product forms the substream "d".

In further preferred plants, the alkylene oxide reactor R1 in the first subplant is a shell-and-tube reactor and/or the alkylene glycol reactor R2 in the second subplant is a tube reactor.

In a further preferred plant, the separation apparatus D has a plurality of stages connected in series, with the alkylene glycol being separated off in the first stage, the dialkylene glycol being separated off in the second stage and the trialkylene glycol being separated off in an optionally present third stage and means for discharging the remaining bottom product from the plant being provided in the last stage; these stages are very particularly preferably rectification columns.

A very particularly energy-efficient plant has a separation apparatus C comprising a plurality of rectification columns connected in parallel or vaporizers connected in series. If rectification columns are used, parts of the reaction mixture discharged from the alkylene glycol reactor are in each case introduced; if vaporizers are used, the reaction mixture discharged from the alkylene glycol reactor is fed into the first vaporizer. In this variant of preferred separation apparatuses, means of utilizing heat energy from the top of at least one rectification column or a vaporizer for heating the bottoms from at least one other rectification column or vaporizer are provided. A person skilled in the art will be familiar with the construction of such energy-efficient groups of columns or vaporizers.

A preferred apparatus according to the invention is shown by way of example in FIG. 1.

A plant comprising a first subplant for preparing alkylene oxide and a second subplant for preparing alkylene glycols is depicted. The first subplant comprises, in the embodiment depicted, an alkylene oxide reactor R1 and also a downstream separation apparatus A and, downstream of this, a separation apparatus B. The second subplant comprises, in the embodiment depicted, an alkylene glycol reactor R2, a downstream separation apparatus C and, downstream of this, a separation apparatus D.

Starting materials for the alkylene oxide reaction (schematically denoted by (EG)) are introduced into the alkylene oxide reactor R1. The product stream P1 from the alkylene oxide reactor R1 is introduced into the separation apparatus A and separated there into a substream "a" comprising essentially $C_2$-$C_6$-olefin and possibly further constituents of the reaction mixture separated off therewith and also a substream "b" containing water, alkylene oxide, alkylene glycol and further components of the reaction mixture and also, if appropriate, organic solvent. Substream "a" is recirculated to the alkylene oxide reactor R1 optionally after separation of the non-olefinic components. Substream "b" is introduced as substream "b2" directly into the separation apparatus B and separated there into a substream "c" comprising essentially alkylene oxide and possibly further constituents of the reaction mixture separated off therewith, a substream "d" containing water, alkylene glycol and further components of the reaction mixture and also, if appropriate, organic solvent and a substream "LM" comprising essentially organic solvent. Substream "LM" is recirculated to the alkylene oxide reactor R1. Substream "c" can be discharged from the plant or is preferably introduced in its entirety or in part as substream "AO1" into the alkylene glycol reactor R2. As an alternative, alkylene oxide from other sources "AO2" can be introduced into the alkylene glycol reactor R2. Substream "b" can, in an alternative embodiment, be conveyed as substream "b1" past the separation apparatus B and introduced directly into the alkylene glycol reactor R2 or substream "b" is divided into a substream "b2" which is introduced into the separation apparatus B and a further substream "b1" which is introduced directly into the alkylene glycol reactor R2.

The product stream P2 from the alkylene glycol reactor R2 is introduced into the separation apparatus C and is separated there into a substream "e" consisting essentially of the water present in the reaction mixture and any further constituents of the reaction mixture separated off with the water, a substream "f" consisting essentially of the organic solvent present in the reaction mixture and any further constituents of the reaction mixture separated off with the organic solvent and a substream "g" made up of the alkylene glycols and the other components of the reaction mixture which have not gone over into substream "e" or substream "f" and also, if appropriate, a substream "eye" containing salts and other solids present in the reaction mixture and/or, if appropriate, a substream "j" containing monoalkylene glycol ethers. Substream f is, if appropriate after further work-up, recirculated to the alkylene oxide reactor R1. Substream "e" and any substream "eye" and/or "j" are discharged from the plant. Substream "e" is fed to a wastewater treatment plant (not shown). As an alternative, substream "e" can be recirculated in its entirety or in part as substream "e1" to the alkylene glycol reactor R2, if appropriate with introduction of fresh water FW. This will be the case particularly when the first plant section is not in operation or is in operation only with a reduced production capacity.

Substream "g" is introduced into the separation apparatus D where the alkylene glycols and any higher alkylene glycol ethers present in this substream are separated. Substreams of various alkylene glycols and if appropriate higher alkylene glycol ethers (shown as P3, P4 and P5), for example substreams of alkylene glycol, dialkylene glycol and higher alkylene glycols, leave the separation apparatus D. Three substreams of materials of value are shown in the Figure; however, depending on the mode of operation of the plant, fewer or more of these substreams can also be produced. In addition, a substream of high boilers P6 is discharged from separation apparatus D.

While the invention has been described in detail, modifications within the spirit and scope of the invention will be readily apparent to those of skill in the art. In view of the foregoing discussion, relevant knowledge in the art and references including co-pending applications discussed above in connection with the Background and Detailed Description, the disclosures of which are all incorporated herein by reference, further description is deemed unnecessary.

What is claimed is:

1. A process for preparing alkylene oxide and an alkylene oxide derivative chosen from the group consisting of alkylene glycols, alkylene glycol ethers and mixtures thereof in an integrated plant having a first subplant for preparing alkylene oxide by reacting $C_2$-$C_6$-olefin with an oxidant in a liquid and water-containing phase, with alkylene glycols being formed as by-products, and a second subplant for preparing an alkylene oxide derivative chosen from the group consisting of alkylene glycols, alkylene glycol ethers and mixtures thereof by reacting alkylene oxide with a ring opening agent chosen from the group consisting of water, alcohols and mixtures thereof in the liquid phase being connected to the first subplant, wherein the reaction mixture which originates from the first subplant and comprises at least water and an alkylene oxide derivative chosen from the group consisting of alkylene glycols, alkylene glycol ethers and mixtures thereof is introduced into the second subplant.

2. The process as claimed in claim 1, wherein the first subplant has at least one alkylene oxide reactor R1 and a first downstream separation apparatus A and an optional second separation apparatus B downstream of A, the separation apparatuses mainly comprising rectification columns, and, connected to the first subplant, a second subplant for preparing alkylene glycols, which has at least one alkylene glycol reactor R2 and at least one third downstream separation apparatus C and at least one fourth separation apparatus D located downstream of the third, wherein the process comprises the following steps:

i) production of alkylene oxide by reaction of $C_2$-$C_6$-olefin with an oxidant in the liquid phase in the first subplant, ii) separation of the reaction mixture leaving the alkylene oxide reactor R1 in the separation apparatus A into a substream a comprising $C_2$-$C_6$-olefin, optionally with further constituents of the reaction mixture which have been separated off with this, and a substream b comprising water, alkylene oxide, alkylene glycol and further components of the reaction mixture and optionally organic solvent, iii) separation of the substream b in the separation apparatus B into a substream c comprising alkylene oxide, optionally with further constituents of the reaction mixture which have been separated off with this, and a substream d comprising water, alkylene glycol and further components of the reaction mixture and optionally organic solvent, iv) production of alkylene glycol and higher alkylene glycols by reaction of alkylene oxide with water in the aqueous phase in the second subplant, by v) introducing the substream b from the separation apparatus A and/or the substream d from the separation apparatus B after adjusting the pH, into the alkylene glycol reactor R2, vi) introducing alkylene oxide from substream c and optionally from other sources into the alkylene glycol reactor R2, with this step being able to be omitted if the substream b from the separation apparatus A is introduced into the alkylene glycol reactor, vii) separating the alkylene glycol- and alkylene glycol ether-containing reaction mixture leaving the alkylene glycol reactor R2 in the separation apparatus C into a substream e consisting essentially of the water present in the reaction mixture and further constituents of the reaction mixture which have been separated off with the water and also additionally a substream f consisting essentially of the organic solvent present in the reaction mixture and further constituents of the reaction mixture which have been separated off with the organic solvent, and a substream g formed by the alkylene glycols and the other components of the reaction mixture which have not gone over into the substream e and not into the substream f and also into a substream i, containing salts and other solids from the reaction mixture, and into a substream j, containing monoalkylene glycol ethers, viii) discharging at least part of the substream e from the plant and recirculating any remaining part of the substream e to the inlet of the alkylene glycol reactor R2, ix) recirculating any substream f present after further processing to the alkylene oxide reactor R1 and x) separating the alkylene glycols present in the substream g in the separation apparatus D.

3. The process as claimed in claim 1, wherein the reaction to form alkylene oxide in the first subplant is carried out in aqueous-alcoholic solution to produce a first reaction product stream comprising at least water, alcohol, alkylene glycols and alkylene glycol ethers, and wherein optionally olefinic starting material and or alkylene oxide produced in the first subplant are removed from the first reaction product stream prior to passage thereof into the second subplant wherein mainly alkylene glycol ethers are formed.

4. The process as claimed in claim 3, wherein the first subplant has at least one alkylene oxide reactor R1 and a first downstream separation apparatus A and an optional second separation apparatus B downstream of A, which mainly comprise rectification columns, and, connected to the first subplant, a second subplant for preparing alkylene glycols, which has at least one alkylene glycol reactor R2 and at least one third downstream separation apparatus C and at least one fourth separation apparatus D located downstream of the third, wherein the process comprises the following steps:

i) production of alkylene oxide by reaction of $C_2$-$C_6$-olefin with an oxidant in the liquid phase in the first subplant, ii) separation of the reaction mixture leaving the alkylene oxide reactor R1 in the separation apparatus A into a substream a comprising $C_2$-$C_6$-olefin, optionally with further constituents of the reaction mixture which have been separated off with this, and a substream b comprising water, alkylene oxide, alkylene glycol and further components of the reaction mixture and optionally organic solvent, iii) separation of the substream b in the separation apparatus B into a substream c comprising alkylene oxide, optionally with further constituents of the reaction mixture which have been separated off with this, and a substream d comprising water, alkylene glycol and further components of the reaction mixture and optionally organic solvent, iv) production of alkylene glycol and higher alkylene glycols by reaction of alkylene oxide with water in the aqueous phase in the second subplant, by v) introducing the substream b from the separation apparatus A and/or the substream d from the separation apparatus B after adjusting the pH, into the alkylene glycol reactor R2, vi) introducing alkylene oxide from substream c and optionally from other sources into the alkylene glycol reactor R2, with this step being able to be omitted if the substream b from the separation apparatus A is introduced into the alkylene glycol reactor, vii) separating the alkylene glycol- and alkylene glycol ether-containing reaction mixture leaving the alkylene glycol reactor R2 in the separation apparatus C into a substream e consisting essentially of the water present in the reaction mixture and further constituents of the reaction mixture which have been separated off with the water and also additionally a substream f consisting essentially of the organic solvent present in the reaction mixture and further constituents of the reaction mixture which have been separated off with the organic solvent, and a substream g formed by the alkylene glycols and the other components of the reaction mixture which have not gone over into the substream e and not into the substream f and also into a substream i, containing salts and other solids from the reaction mixture, and into a substream j, containing monoalkylene glycol ethers, viii) discharging at least part of the substream e from the plant and recirculating any remaining part of the substream e to the inlet of the alkylene glycol reactor R2, ix) recirculating any substream f present after further processing to the alkylene oxide reactor R1 and x) separating the alkylene glycols present in the substream g in the separation apparatus D.

5. The process as claimed in claim 4, wherein, in the first subplant, propylene is catalytically reacted with a peroxide or hydroperoxide in an aqueous or aqueous-alcoholic phase to form propylene oxide.

6. The process as claimed in claim 5, wherein at least one flash vessel or vaporizer is used as separation apparatus A and at least one rectification column is used as separation apparatus B, with at least part of the alkylene oxide being taken off at the top, part of the alkylene oxide being taken off as side offtake stream and a bottom product forming the substream d.

7. The process as claimed in claim 4, wherein the production of alkylene glycol and of higher alkylene glycols is carried out by catalytic reaction of alkylene oxide with water in an aqueous phase in the alkylene glycol reactor, with an acid or an acidic ion exchanger being used as catalyst.

8. The process as claimed in claim 4, where the substream b is separated in the separation apparatus B into a substream c and a substream d, the substream d and at least part of the substream c are conveyed from the separation apparatus B into the alkylene glycol reactor R2, and in which, the substream d from the separation apparatus B is combined with part of the substream e from the separation apparatus C before being introduced into the alkylene glycol reactor R2.

9. The process as claimed in claim 4, wherein the fractionation of the reaction mixture containing alkylene glycols leaving the alkylene glycol reactor R2 in the separation apparatus C is carried out in such a way that the substream e consists essentially of the water present in the reaction mixture and other constituents of the reaction mixture.

10. The process as claimed in claim 9, wherein the separation apparatus C comprises a plurality of rectification columns which are connected in parallel, where, in the rectification columns connected in parallel, in each case parts of the reaction mixture discharged from the alkylene glycol reactor R2 are introduced, with heat energy from the top of at least one rectification column being utilized for heating the bottom of at least one other rectification column and the rectification columns being operated at different pressures so that the overhead product in each case comprises water.

11. The process as claimed in claim 9, wherein the separation apparatus C comprises a plurality of vaporizers connected in series, with the heat of condensation of the vapor stream leaving at least one vaporizer being utilized for heating the next vaporizer and the vaporizers being operated at different pressures so that the overhead product in each case comprises water.

12. The process as claimed in claim 3, wherein a separation apparatus D for alkylene glycol having a plurality of stages connected in series is used, with the alkylene glycol being separated off in the first stage, the dialkylene glycol being separated off in the second stage and the trialkylene glycol being separated off in an optionally present third stage, and the remaining bottom product being discharged from the plant.

13. The process as claimed in claim 2, wherein at least part of substream e is introduced into a wastewater purification plant.

14. The process as claimed in claim 4, wherein at least part of substream e is introduced into a wastewater purification plant.

15. The process as claimed in claim 5, wherein the peroxide is hydrogen peroxide.

16. The process as claimed in claim 7, wherein the production of alkylene glycol and of higher alkylene glycols is carried out by catalytic reaction of alkylene oxide with water in an acidic aqueous phase in the alkylene glycol reactor.

17. The process as claimed in claim 9, wherein substream e consists essentially of the water present in the reaction mixture as well as ethers which have been formed from parts of the alkylene oxide and other constituents of the reaction mixture.

18. The process as claimed in claim 10, wherein the separation apparatus C further comprises at least one downstream rectification column.

19. The process as claimed in claim 10, wherein the overhead product in each case further comprises at least one organic constituent selected from the group consisting of ethers, residues of organic solvent, and residues of alkylene glycol.

20. The process as claimed in claim 11, wherein the overhead product in each case further comprises at least one organic constituent selected from the group consisting of ethers, residues of organic solvent, and residues of alkylene glycol.

21. The process as claimed in claim 18, wherein the combined overhead products from the rectification columns connected in parallel are introduced into the at least one downstream rectification column, in which water present therein is separated off.

22. The process as claimed in claim 12, wherein the plurality of stages is formed from rectification columns.

* * * * *